(12) United States Patent
Evelyn et al.

(10) Patent No.: US 11,738,149 B2
(45) Date of Patent: Aug. 29, 2023

(54) DETACHABLE MEDICAL DEVICE SYSTEM

(71) Applicant: Alerje, INC., Detroit, MI (US)

(72) Inventors: Javier Evelyn, Detroit, MI (US); William Hunter Martin, Detroit, MI (US); Nathan Ivy, Clarendon Hills, MI (US)

(73) Assignee: Alerje, Inc., Detroit, MI (US)

( * ) Notice: Subject to any disclaimer, the term of this patent is extended or adjusted under 35 U.S.C. 154(b) by 0 days.

(21) Appl. No.: 17/321,989

(22) Filed: May 17, 2021

(65) Prior Publication Data

US 2021/0268191 A1 Sep. 2, 2021

Related U.S. Application Data

(63) Continuation of application No. 16/485,066, filed as application No. PCT/US2018/018031 on Feb. 13, 2018, now Pat. No. 11,007,321.

(Continued)

(51) Int. Cl.
*A61M 5/20* (2006.01)
*H04B 1/3827* (2015.01)
(Continued)

(52) U.S. Cl.
CPC ........... *A61M 5/2033* (2013.01); *A61B 50/30* (2016.02); *A61M 5/44* (2013.01);
(Continued)

(58) Field of Classification Search
CPC ...... H04B 1/38; H04B 1/3827; H04B 1/3888; H04B 7/00; A61M 5/20; A61M 5/2033; A61M 5/44; A61M 50/30
See application file for complete search history.

(56) References Cited

U.S. PATENT DOCUMENTS 8,639,288 B1 * 1/2014 Friedman ................ A61M 5/31
455/575.8
8,833,379 B1 9/2014 Kaplan
(Continued)

FOREIGN PATENT DOCUMENTS

CA 2835389 A1 * 11/2012 ........ A61M 5/14244
CN 104411349 A 3/2015
(Continued)

OTHER PUBLICATIONS

International Search Report dated May 24, 2018, Application No. PCT/US2018/018031.
(Continued)

*Primary Examiner* — Blane J Jackson
(74) *Attorney, Agent, or Firm* — The Dobrusin Law Firm, PC

(57) ABSTRACT

A case for a mobile device including a back section and a first front section and a second front section, the first front section being adapted for connection to and separation from the second front section and the back section including an opening for receiving a mobile device; a receiving space located within the first front section and second front section for receiving an injection device, wherein the injection device is at least partially visible when the second section is detached from the first section; a release latch located on one or more of the first front section and second front section for facilitating separation of the second front section from the first front section; and a connector portion for connecting the back section to the first and second front sections.

20 Claims, 13 Drawing Sheets

Related U.S. Application Data

(60) Provisional application No. 62/586,274, filed on Nov. 15, 2017, provisional application No. 62/547,199, filed on Aug. 18, 2017, provisional application No. 62/527,520, filed on Jun. 30, 2017, provisional application No. 62/506,829, filed on May 16, 2017, provisional application No. 62/468,657, filed on Mar. 8, 2017, provisional application No. 62/458,223, filed on Feb. 13, 2017.

(51) Int. Cl.
*A61B 50/30* (2016.01)
*A61M 5/44* (2006.01)

(52) U.S. Cl.
CPC ............... *A61M 2205/3368* (2013.01); *A61M 2205/3569* (2013.01); *A61M 2205/3576* (2013.01); *A61M 2205/36* (2013.01)

(56) References Cited

U.S. PATENT DOCUMENTS

| | | | |
|---|---|---|---|
| 9,250,111 | B2 | 2/2016 | Whalley et al. |
| 9,374,120 | B1* | 6/2016 | Halloran ................ A61F 17/00 |
| 2002/0050462 | A1 | 2/2002 | Penney |
| 2009/0024112 | A1* | 1/2009 | Edwards ................ G16Z 99/00 |
| | | | 604/890.1 |
| 2009/0128330 | A1* | 5/2009 | Monroe ................ G16H 20/17 |
| | | | 340/568.1 |
| 2014/0216976 | A1 | 8/2014 | Conarro |
| 2014/0216979 | A1 | 8/2014 | Veltrop et al. |
| 2014/0228082 | A1* | 8/2014 | Morrow ................ H04B 1/3888 |
| | | | 455/575.8 |
| 2015/0080806 | A1 | 3/2015 | Pribitkin |
| 2015/0328411 | A1 | 11/2015 | Friedman |
| 2016/0310680 | A1 | 10/2016 | Kataoka |
| 2018/0001015 | A1* | 1/2018 | Ziegner ................ B65D 81/3816 |

FOREIGN PATENT DOCUMENTS

| | | | |
|---|---|---|---|
| CN | 105813684 A | 7/2016 | |
| WO | WO-2013154954 A1 * | 10/2013 | ............ A61M 5/20 |
| WO | 2016/107794 A1 | 7/2016 | |
| WO | 2015/115326 A1 | 3/2017 | |

OTHER PUBLICATIONS

European Supplementary European Search Report dated Jul. 27, 2020, Application No. 18750854.4.
Japan Office Action dated Nov. 12, 2021, Application No. 2019-564376.
China Notice of First Office Action dated Mar. 23, 2022, Application No. 201880011414.0.
India First Examination Report dated Jan. 11, 2022, Application No. 201917032263.
Chinese Second Office Action dated Aug. 5, 2022, Application No. 201880011414.0.
Australia Examination Report dated Jul. 26, 2022, Application No. 2018219427.

* cited by examiner

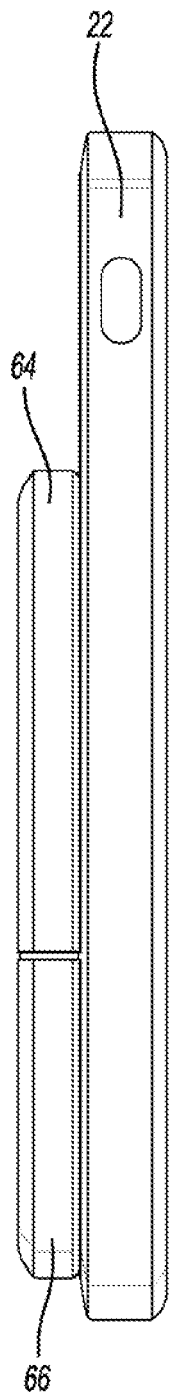
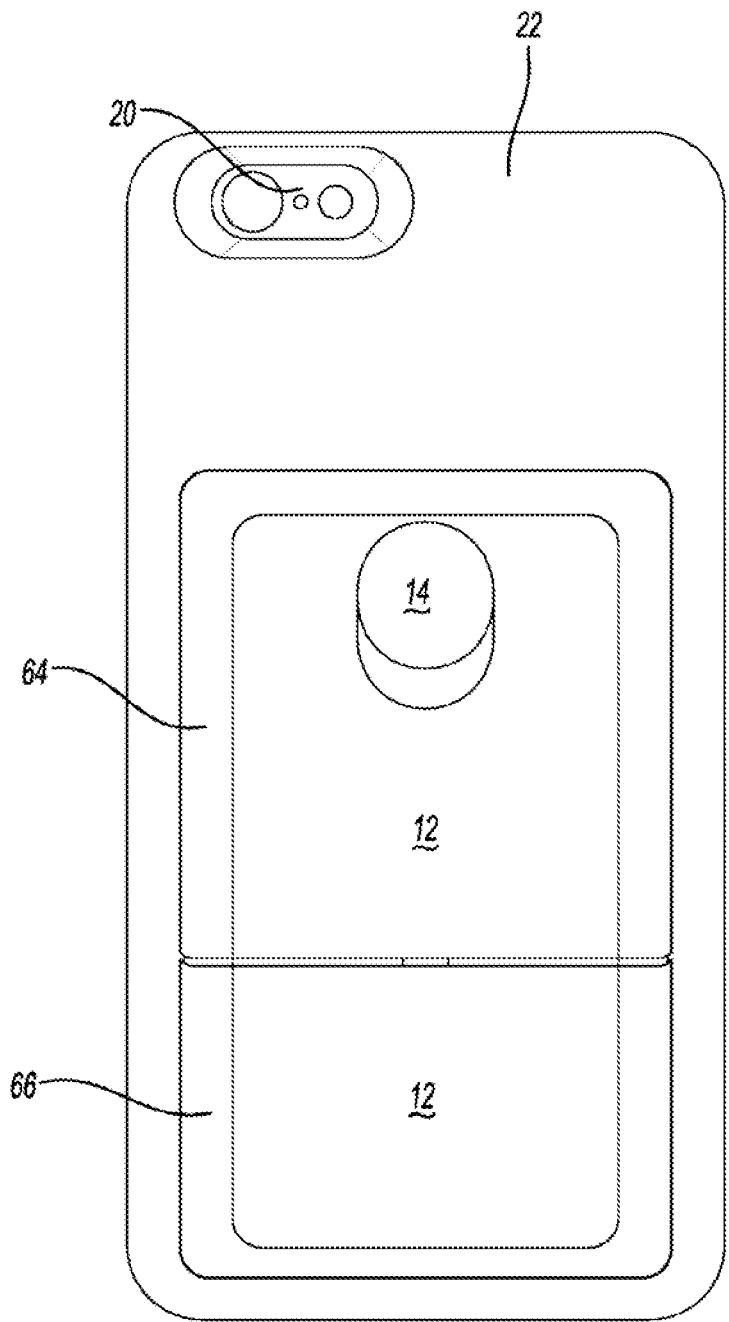
Fig-16A
Fig-16B

DETACHABLE MEDICAL DEVICE SYSTEM

TECHNICAL FIELD

The present teachings are directed to medical devices for connection to and integration with mobile devices. More specifically, the present teachings relate to auto-injection devices for connecting to a mobile device.

BACKGROUND

Epinephrine auto-injectors (EAI) are life-saving medical devices used by the over 15 million Americans that suffer from food allergies during an anaphylactic reaction. An epinephrine auto injector (EAI) is an emergency injection ("shot") of epinephrine. This medicine is used for life-threatening allergic reactions such as severe swelling, breathing problems, or loss of blood pressure. Allergic, or anaphylactic reactions can be caused by stinging and biting insects, allergy injections, food, medicines, exercise, or other known and/or unknown causes.

EAIs are normally stored in individual protective cases in doses of 0.15 mg to 0.3 mg depending on written prescription. Due to the various responses that patients have from the use of the medication, it is recommended to carry two EAIs.

Similarly, injections of insulin or other medications may be required by the over 30 million people in the United States that suffer from diabetes. Without the injection of insulin, a diabetic may experience severe hypoglycemia, or diabetic shock, which can be life threatening. Therefore, diabetics carry insulin on their person in case of low blood sugar. Insulin is available in an auto injector cartridge for quick use. However, insulin must be stored between 56° F. and 80° F. for cartridges which are in current use. Because insulin injections are required by a large proportion of people with diabetes, it is necessary to keep insulin nearby at all times.

Inhalers are medical devices used for delivering medication into the body via the lungs. The inhalers may release a medication in aerosol, powder, or liquid form. The inhalers may release the medication in metered doses (i.e., releases a fixed dose of the medication per each use). Inhalers may be used to treat asthma, influenza, allergies, chronic obstructive pulmonary disease, and the like. Inhalers may be used on a set dosage/time interval or in emergencies, such as during an asthma attack. Thus it is recommended users of inhalers carry an inhaler or have one in close proximity. Some types of inhalers provide metered doses of medication.

A common issue is that auto injectors and inhalers may not be readily available when needed. Another issue is that auto injectors and inhalers may expire without the knowledge of the user. A further issue with inhalers may be that the user is unaware how many doses are left for use. In addition, there are often caregivers, including physicians, nurses and family members who wish to monitor medication use of an individual, especially when that individual is a child or someone who is elderly.

Based upon the foregoing concerns, it would be useful to develop a means by which an auto injector and/or inhaler may be consistently available to a user. It would further be useful to notify the user of expiration, remaining doses, or other information about the auto injector and/or inhaler.

SUMMARY OF THE INVENTION

The present teachings effectively resolve the aforementioned deficiencies by providing a device for connecting a medical device (e.g. auto-injector, inhaler, or other medical treatment device/container) to a mobile device. The device described herein not only attaches to a mobile device but is capable of sharing information with a mobile device to which it is connected (e.g. via Bluetooth, Wi-Fi, near field communication (NFC), or some combination thereof).

The teachings herein provide for a mobile device accessory system comprising a case portion, the case portion including a back section and a first front section and a second front section, the first front section being adapted for connection to and separation from the second front section and the back section including an opening for receiving a mobile device, a receiving space located within the first front section and second front section for receiving an injection device, wherein the injection device is at least partially visible when the second section is detached from the first section, a release latch located on one or more of the first front section and second front section for facilitating separation of the second front section from the first front section, and a connector portion for connecting the back section to the first and second front sections.

The teachings herein further provide that the release latch may comprise a button portion. The back section may include an edge that engages in a friction fit with a mobile device. One or more of the back section and first and second front sections may be formed of a heat-resistive material. The system may include a communication device to communicate with an application or software on a computing device. The first and second front sections may be removably attached to the back section. The connector portion may be adapted to directly contact the first front section. The connector portion may be free of any direct contact with the second front section. The first and second front sections may be connected to one another via a friction fit. The first and second front sections may be connected to one another via a mechanical fastener.

The release latch may slide from a first position to a second position so that the first and second front sections are separated from one another. The release latch may be depressed to separate the first front section from the second front section. The release latch may be located on the first front section.

The system may include one or more vent portions. The system may include a locking device for maintaining the injection device within the first and second front portions until accessed. The system may include a temperature sensor. The system may include a mobile application. The mobile application may be adapted for one or more oft permitting access to the injector; notifying a user's care circle if the injector has been accessed; notifying a user if the medication within the injector is expired; notifying a user if the injector has malfunctioned; or notifying a user if the temperature within the case portion exceeds a pre-determined temperature limit.

It is also possible that a portion of the device that contacts the injector may comprise a polyethylene terephthalate, a polypropylene, polyamide, polyethylene, an aerogel, a silicone, a metallized polyethylene terephthalate, a metallized polypropylene, a metallized polyamide, a metalized polyethylene or some combination thereof. The connector portion may include a mechanical fastening means, and adhesive fastening means, a magnetic fastening means or some combination thereof. The injector may include more than one dose of medication.

The teachings herein also envision a method for forming a mobile device case comprising providing first and second separable front sections, separating the first and second front sections, locating an injector into one or more of the first and second front sections, connecting the first and second front sections to one another, and attaching a back section to first and second front sections, wherein the back section is in direct contact with the first front section.

The method may also include locating a mobile device into direct contact with the back section. The method may include separating the first and second front sections from one another to access the injector.

The present teachings are further directed to a detachable medical device, such as an auto-injector or other medication-containing device, sized to fit into a smartphone case which will communicate with a mobile application via radio frequency based technology (e.g. Bluetooth, wi-fi, NFC). In the event that the device is used during a life-threatening emergency, the assisting mobile application may send alert messages to emergency services as well as a user's "Care Circle" (family, friends, caregivers, medical professional, etc.) that will include their current location. Furthermore, users may be sent push notifications whenever the medication is approaching its expiration date to meet patient adherence.

In an effort to address maintaining the thermostability of the medication located within the medical device, the material of the device for connecting the medical device to the mobile device may be selected to assist in protecting the medicine (e.g. epinephrine, insulin, and the like) from extreme weather conditions (heat, cold, humidity, precipitation). The material for forming the device may be a polymeric material, a carbon-based material, the like, or a combination thereof. More specifically it may be polyethylene terephthalate material, such as a metallized polyethylene terephthalate (MPET) or a graphite material, such as a pyrolytic graphite sheet (PGS). A phase change material (PCM) may be used with the MPET, PGS, or a combination thereof. The device may be formed so that multiple layers of the material for protecting the medical device will be placed around the medical device. The medical device may be shaped to fit on the back of any mobile device. It is possible that one attachment device may be adjustable to fit a variety of mobile device. Alternatively, it may also be possible that the attachment devices are shaped to fit a specific brand and/or model of mobile device. The attachment device may be formed as a mobile device case in that it would replace a traditional mobile device case. It is also possible that the attachment device may be formed to fit onto an existing mobile device case.

BRIEF DESCRIPTION OF THE DRAWINGS

FIG. 16A is a side profile view of an exemplary phone case in accordance with the present teachings.

FIG. 16B is a top down view of the phone case of FIG. 16A.

DETAILED DESCRIPTION

Figure 1:
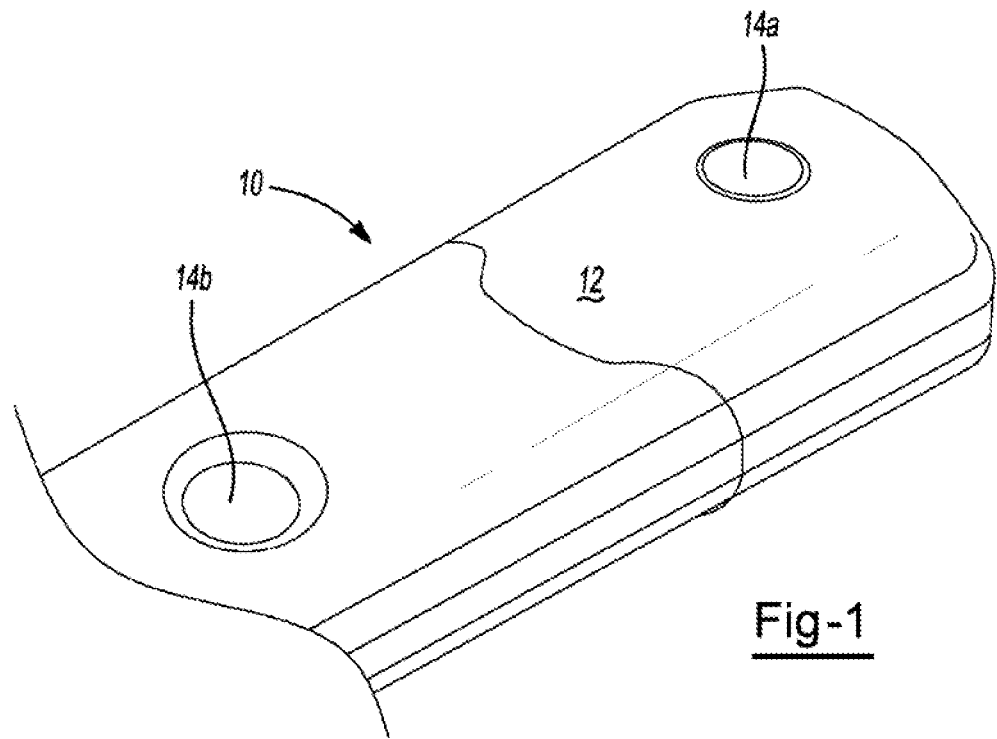
FIG. 1 shows a portion of an exemplary phone case in accordance with the present teachings.

The present teachings meet one or more of the above needs by the improved devices and methods described herein. The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application claims the benefit of the filing dates of United States Provisional Application Nos. 62/458,223, filed Feb. 13, 2017; 62/468,657, filed Mar. 8, 2017; 62/506,829, filed May 16, 2017; 62/527,520, filed Jun. 30, 2017; 62/547, 199, filed Aug. 18, 2017; and 62/586,274, filed Nov. 15, 2017, the contents of these applications being hereby incorporated by reference for all purposes.

The teachings herein are directed to a device for facilitating the carrying of a medical device in concert with a mobile device. The medical device may be any medical device carrying fast-acting or necessary medicine. The medical device may contain temperature sensitive material. The medical device may include an epinephrine auto injector (EAI), an inhaler, an insulin auto-injector (IAI), and/or the like. The epinephrine or other medication may be in the form of a nasal spray. More particularly, the teachings are directed to an attachment device capable of attaching to a mobile device that includes a space for holding a medical device, which may be an EAI, an inhaler, an IAI, or the like. The medical device may be integrated into the attachment device. The medical device may be removably attachable to the attachment device mobile devices may include computing devices small enough to be held and operated by a hand of an individual, include mobile technology which uses radio waves to transmit and receive data (e.g., 3G, 4G, Bluetooth, wi-fi, near field communication). Mobile devices may include mobile phones, smartphones, tablet computers, the like, or any combination thereof.

The teachings herein provide for a mobile device accessory system comprising a case portion. The case portion may include a back section and a front portion or cover. The front portion may include a first front section and a second front section, the first front section being adapted for connection to and separation from the second front section and the back section including an opening for receiving a mobile device. A receiving space may be located within the first front section and second front section for receiving an injection (or other medication) device, wherein the injection device is at least partially visible when the second section is detached from the first section. A release latch or button (which may be spring loaded) is located on one or more of the first front section and second front section for facilitating separation of the second front section from the first front section. A connector portion may be present for connecting the back section to the first and second front sections.

The teachings herein further provide that the release latch may comprise a button portion. The back section may include an edge that engages in a friction fit with a mobile device. The first and second front sections may be removably attached to the back section. The connector portion may be adapted to directly contact the first front section. The connector portion may be free of any direct contact with the second front section. The first and second front sections may be connected to one another via a friction fit. The first and second front sections may be connected to one another via a mechanical fastener.

The release latch may slide from a first position to a second position so that the first and second front sections are separated from one another. The release latch may be depressed to separate the first front section from the second front section. The release latch may be located on the first front section.

The attachment device described herein may also take into consideration additional accessories that may be utilized with a mobile device (for example, headphones, wireless charging device, cases, or other accessories). For example, the attachment device may be a smart phone case. The smart phone case may include a front cover which is foldable. The front cover may be detachable from the phone case. The foldable front cover may be configured as a wallet to hold identification cards, credit cards, health insurance cards, cash and the like.

Further, in an attempt to protect the medical device or medication located therein from environmental factors, specific materials may be utilized in forming the attachment device. It is also possible that the medical device itself may include a coating or wrap of a material selected to protect it from environmental factors. As one specific example, in an effort to address the thermostability of the medication, materials such as MPET, PGS, PCM, aerogel (e.g., silica or metal oxide aerogels), BoPET, silicone or a combination thereof may be utilized for forming the attachment device. In addition, or as an alternative method, each medical device may be wrapped in the MPET, PGS, PCM, aerogel, BoPET, silicone or a combination of thereof. For example, the MPET may be used to reflect thermal radiation from the surrounding environment of the attachment device, the wrap, or both. The PGS may be used to disperse thermal energy throughout the attachment device, the wrap, or both. Additionally, the MPET and the PGS may be combined with a PCM, which may be used to store and dissipate thermal energy based on the phase change characteristics of the material. The combination of the MPET, PGS, and PCM contribute to the regulation of the temperature of the medical device, such that the medical device does not exceed or fall below the prescribed storage range, preventing the decomposition of the medicine within the medical device. The materials may be layered to maximize the thermal characteristics to provide the most consistent temperature range for storing the medical device.

The attachment device may also be fitted with a communication device to allow communication between the attachment device and the mobile device to which it is attached (or alternatively another mobile device). It is possible that the medical device located into the attachment device may be scanned by a mobile device prior to locating the medical device within the attachment device. This scanning may proceed with the assistance of a mobile application. By scanning the medical device, the mobile application may recognize and save relevant information such as registration numbers, expiration date, dosage amount, storage requirements, the like, or a combination thereof. For example, the scanned information may include a medical device's registration number, the expiration date of the medicine within the medical device, and the dosage amount of the medical device.

The attachment device may allow for communication with emergency services, contacts of the users, or both. The attachment device may detect an emergency contact indicator. The emergency contact indicator may include removal of the medical device, a user attempting to remove the medical device, or both. Upon detecting the emergency contact indicator, the attachment device in combination with the mobile application may initiate contacting emergency services, contacts of the users, or both. Contacting may include sending a signal to the mobile device to which the attachment device is affixed to, such as through BLE, wi-fi, NFC, or similar technology. Contacting may include instructing the mobile device to contact emergency services and/or emergency contacts, such as through BLE, wi-fi, NFC, or similar technology. Emergency services may include emergency dispatching services, such as 911 and other international equivalents. Emergency contacts may include family, friends, caregivers, medical professionals pre-identified by the user as emergency contacts, such as the users "Care Circle". Any communication or signals between the attachment device, mobile device, emergency services, and/or emergency contacts may be compliant with the Health Insurance Portability and Accountability Act (HIPAA compliant). To be HIPAA compliant, the communication or signals may be sent via any communication platform or protocol which is HIPAA compliant, such as the Rapid-SOS™ platform. Additionally, the mobile application may provide the user with referrals to medical professionals nearby. For example, the mobile application may refer a user with food allergies to an allergist that is within a specified distance from the user's location.

Users may also be sent push notifications whenever the medication is approaching its expiration date to meet patient adherence. Training videos on how to use the medical device (e.g. an EAI, an IAI, an inhaler, or the like) may also be included in the notification.

Users may also create food allergy profiles for themselves as well as their family/household. The profile may preferably include what an individual is specifically allergic to. The mobile application may then allow users to share the profiles with all necessary parties (schools, other parents/guardians, events, etc.).

The mobile application may also allow users to scan foods while shopping to determine if they, or anyone else in their family is allergic to a given item. To scan the foods, the user targets and scans the UPC barcode on a product. Once scanned, the mobile application searches for the product's full ingredients list and immediately displays the full list of ingredients, including allergens, in the product.

The mobile application allows the user to create a curated list of allergy-filtered recipes. The mobile application provides a searching function which allows the user to select a type of recipe and then filter the list of recipes by specific allergies. Once the user selects a desired recipe, the recipe details populate on the screen to show the user the ingredients. The selected recipe may also include a link to a website for further information about the recipe, such as preparation instructions. If the user decides the recipe is worth keeping, the mobile application allows the user to save the recipe in the application for later use and further, delete recipes from the list which the user no longer wishes to save.

The attachment device (e.g., phone case), the medical device, or both may include one or more sensing devices. The sensing devices may sense one or more physical conditions of the medical device, such as temperature, presence, installation, removal or use of the medical device. The sensing devices may sense the amount of a medication used and/or available within the medical device. The one or more sensing devices may communicate with a mobile device, such as through wireless technology (e.g., BLE, wi-fi, NFC, or similar technology). The mobile device may then use the information to track usage of the medical device, determine doses used of the medical device, and/or determine doses remaining in the medical device. The one or more sensing devices may include one or more cartridge sensors, temperature sensors, the like, or combination thereof.

The attachment device, medical device, or both may include one or more subsystems. Subsystems may include an electronics system, communication system, thermal maintenance system, security system, or any combination thereof.

An electronics system may include one or more microcontrollers, power sources, circuit boards, fuses, switches, sensing devices, the like, or any combination thereof. The one or more microcontrollers may be an N-bit microcontroller, such as an 8-bit, 32-bit, or the like. The one or more microcontrollers may have or be attached to one or more peripherals, such as a Universal Asynchronous Receiver Transmitter (UART), Universal Synchronous/Asynchronous Receiver Transmitter (USART), Inter-integrated circuit (I2C), Analog to Digital Converter (ADC), the like, or any combination thereof. The one or more sensing devices may include one or more temperature sensors. The temperature sensor may be any device capable of sensing and/or determining a temperature of the medical device or medication within the medical device. The one or more temperature sensors may include an analog sensor, digital sensor, diode sensor, thermistor sensor, resistive temperature detector, the like, or any combination thereof. The one or more sensing devices may include a medical device sensor. The medical device sensor may be any sensor capable of sensing introduction, presence, and/or removal of a medical device. The medical device sensor may include a switch contact, optical beam break, capacitive sensor, inductive sensor, the like, or any combination thereof. The one or more power sources may be any power source capable of power the device or connecting the device to a power source. The one or more power sources may have any power or life expectancy suitable for use. The one or more power sources may include a coin cell, a rechargeable battery, charging circuitry, the like, or any combination thereof. The one or more fuses and/or switches may include one or more thermal fuses, thermal switches, or both. The thermal fuse or switch may be any fuse or switch capable of preventing overheating of the device, the medical device, or both. The thermal fuse and/or thermal switch may be a one-time use or multiple-use fuse or switch. The thermal fuse and/or thermal switch may be reset manually or automatically.

A thermal subsystem may include any system capable of maintaining a temperature condition of the medical device such that the medication is not exposed to certain temperature conditions (e.g., extreme hot or cold which impacts effectiveness of the medication). The thermal subsystem may function to reflect and dissipate heat and radiation from the medical device. The thermal subsystem may prevent heat transferring from a mobile device to the medical device. The thermal subsystem may include one or more materials of the attachment device, one or more physical characteristics of the attachment device, one or more heat exchangers, or a combination thereof. The one or more materials may have a low thermal conductivity. The one or more materials may have a light color to reduce heat absorption. A holding area (i.e., cartridge cavity) may be lined with a heat resistant material, such as the MPET or PGS. The MPET and/or PGS may include a PCM, which thermally stores and releases energy in a pre-determined temperature range to provide thermostability within the target temperature range for the storage of the medical device. The PCM may be salt hydrates, petroleum based material, biobased material, or a combination thereof. The thermal subsystem may be arranged in layers for providing consistent thermostable temperature, utilizing the different properties of the different materials. The thermal subsystem may include one or more heat exchangers.

The one or more heat exchangers may include one or more venting systems, such as vent ports; one or more Peltier devices, one or more fans, the like, or any combination thereof. The one or more heat exchangers may actively monitor and maintain the temperature within the holding area. The material choice and layering, in combination with the one or more heat exchangers may provide superior temperature regulation. The phone case includes a plurality of venting ports. The venting ports are located between the holding area and the mobile device. The venting ports allow for heat dissipation from the mobile device such that the heat is not transferred to a medical device within the holding area.

The phone case includes a mobile device and a medical device holding area. The medical device holding area is able to receive or hold part of a medical device, such as a cartridge for an auto-injector or at least part of an inhaler. Adjacent to and in contact with the holding area are a cartridge sensor, thermal fuse, and temperature sensor. The cartridge sensor is able to sense the presence and/or removal of a medical device. The cartridge sensor may be able to sense a fully seated or installed position of the medical device so that a user knows the medical device is proper seated within the case. The temperature sensor is able to sense a temperature or other physical condition of the medical device and/or surroundings of the medical device. The case may include an independent power source or be affixed to a power source. The power source may include a battery. Alternatively, or in combination with an independent power source, the case may be powered by the mobile device. The case includes a microcontroller, radio frequency transmitter and receiver, and battery mounted onto a printed circuit board (PCB).

The cartridge security system includes a back panel located over and covering the holding area for a medical device. The back panel is affixed to the exterior of the phone case via a slide lock. The slide lock is spring-loaded. The back panel or the phone case may include tabs which further align and engage the back panel with the phone case. A seal may be located about the opening for the holding area or about the back panel. The seal may prevent entry of contaminants into the holding area.

The attachment device (e.g., phone case), medical device, or both may include a security system. The security system includes a system which may allow for insertion and removal of a medical device from the attachment device, prevent accidental removal of the medical device, and/or may be child/tamper proof. The security system may include one or more doors and or panels which allow insertion or removal of a medical device. The security system may include one or more locking mechanisms to maintain the one or more doors and or panels closed. One or more locking mechanisms may include a slide lock, spring loaded slide lock, a button, a multi-step button, the like, or any combination thereof. The one or more security systems may include one or more springs to facilitate removal of the medical device from the attachment device. For example, the security system is a multi-step button, where upon depressing the button to the first step releases the medical device holder from the phone case and further depressing the button to the second step shoots the needle of an auto-injector out of the medical device holder such that a user would be able to administer the emergency medicine. The security system may be mechanical, electromechanical, or electrical. The security system may only be mechanical to avoid reliance on a power source. The security system may form a seal around a holding area. The seal may prevent contaminants (e.g., dust, dirt, debris, moisture, liquids) from entering the holding area to ensure the medical device is sanitary.

The communication system may include one or more wired or wireless communications systems. The one or more wired or wireless communications systems may include any radio frequency based transmitter or receiver, such as a wi-fi transmitter and receiver, a Bluetooth transmitter and receiver, Bluetooth low energy (BLE) transmitter and receiver, near field communication (NFC) transmitter and receiver, or the like.

After releasing the injector, a 10 second countdown may occur, using radio frequency based technology, the mobile app sends their location data immediately to emergency services no matter where they are, and works internationally where 911 is not the emergency number. This also action initiates the interaction of the phone case with the supporting mobile application which alerts the users "Care Circle" of the incident. If the medical device is unlocked from the device and is not used, the user can disable the alerts and phone call with the tap of a button. Furthermore, during non-emergencies the medical device could be put back onto the back of the phone case.

In an effort to provide for safe use of the attachment device and associated medical device, the device may be designed to utilize a two-factor authentication. For example, two buttons on the phone case may need to be pressed in order to release the medical device.

The medication may be separated from the phone case and yet still in communication with and having the same functionality as if still within the phone case. For example, the medication may be located on a keychain.

The medication may be injected via a needle. The needle may deliver medication from an auto-injector to a user. The needle may be a bent needle design. The bent needle design may allow for compact space usage of the case by the needle. The needle is includes a bevel at the end of a shaft. The shaft bends at generally perpendicular angle, such as toward the medical device within the phone case. Generally perpendicular to the bevel is a force receiving portion of the needle. The force receiving portion may be affixed to a spring. The spring is able to transmit force a user applies to the phone case in case of an emergency to project the bevel portion of the needle outside of the phone case and into the user to allow transmission of the medication. After the spring projects the needle outside of the case, a receiving portion of the shaft is placed in communication with the medication to be dispensed.

Figure 2:
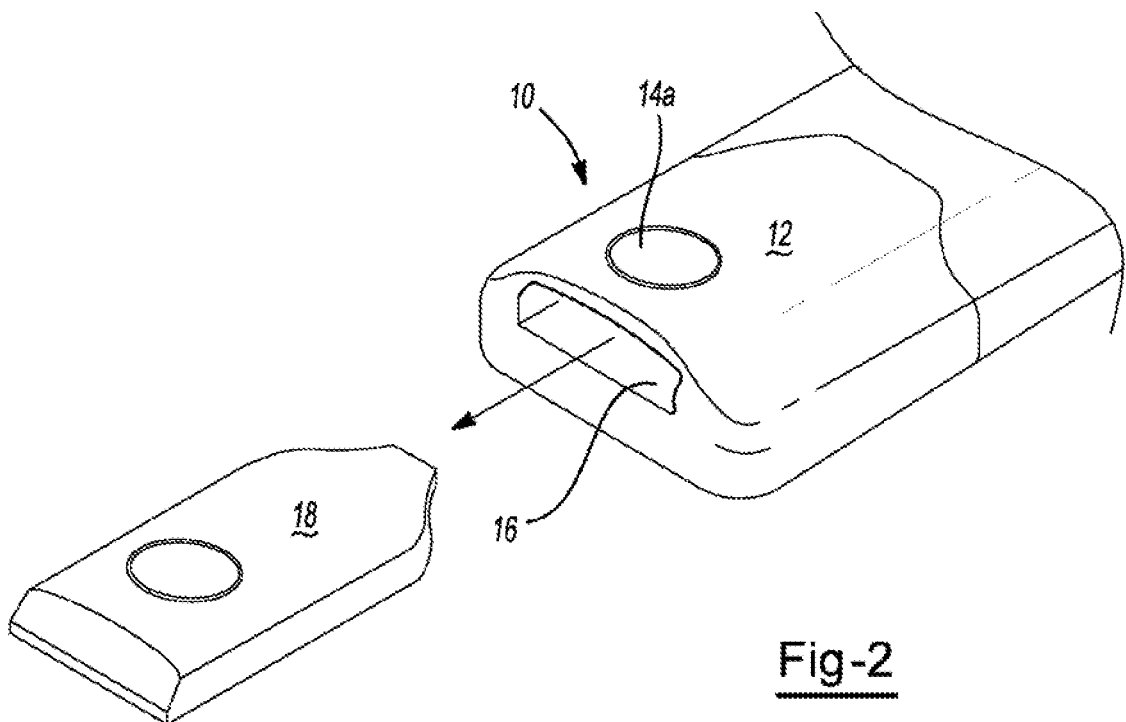
FIG. 2 shows an exemplary injector being removed from the phone case of FIG. 1.

FIG. 1 shows a phone case 10 including a cover 12 for covering the injector (e.g., the medication). It displays two release latches 14a, 14b. Both release latches or "buttons" would have to be pressed at the same time to unlock the medical device. FIG. 2 illustrates an auto-injector 18 being detached from the phone case 10, and the cover 12 for covering the injector. An opening 16 for receiving the injector is also shown.

Figure 3:
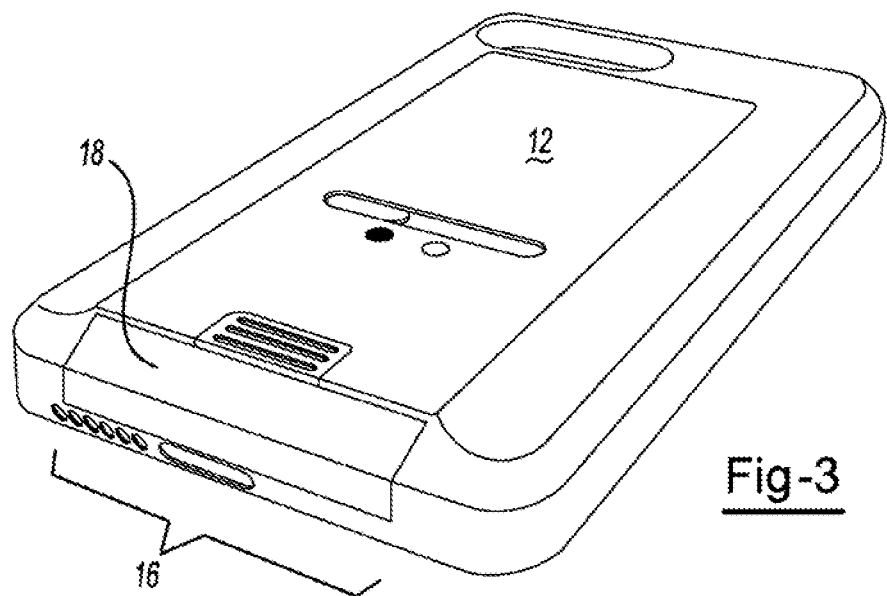
FIG. 3 shows a perspective view of an exemplary phone case in accordance with the present teachings.
Figure 4:
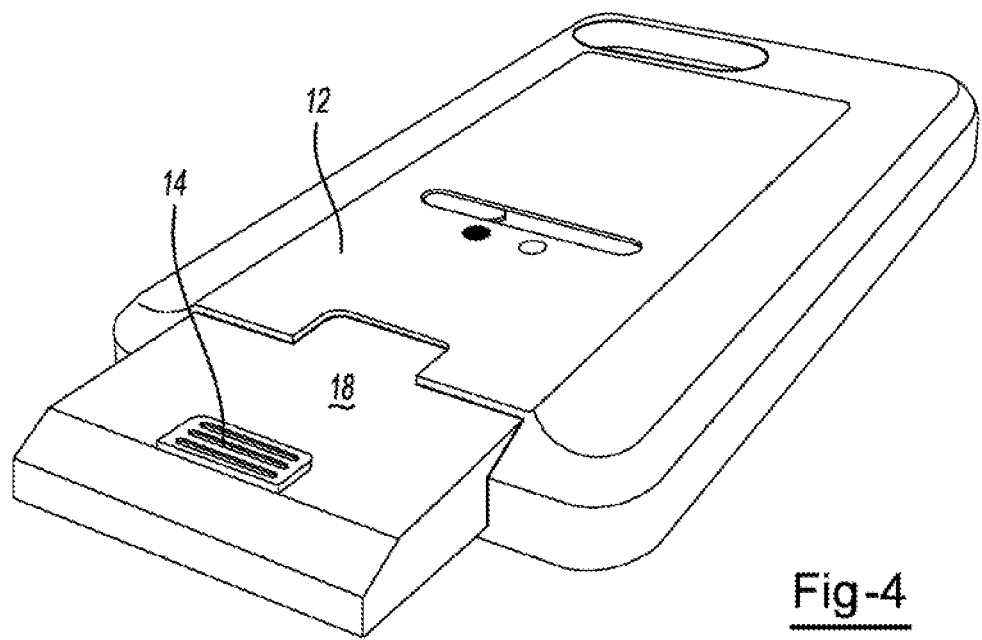
FIG. 4 shows the phone case of FIG. 3 as the injector is being ejected
Figure 5:
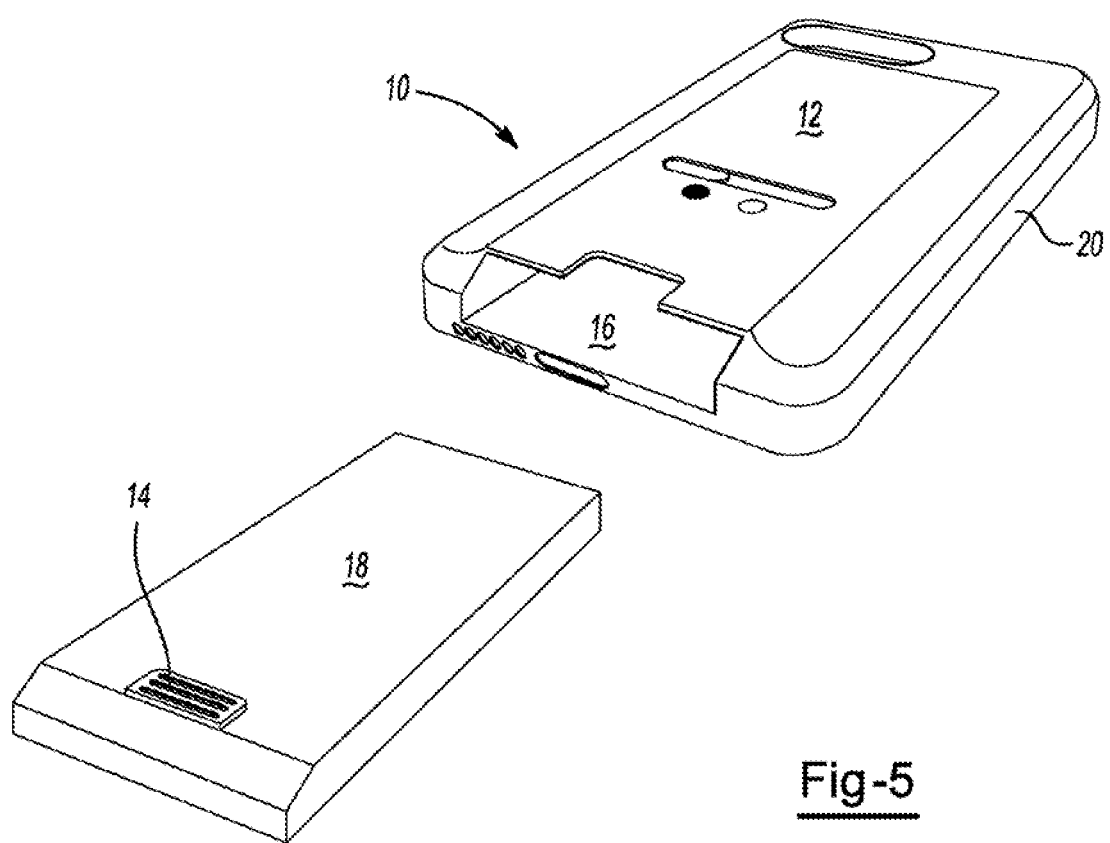
FIG. 5 shows an exemplary injector being removed from the phone case of FIG. 3.

FIGS. 3, 4 and 5 illustrate a phone case including a cover 12 for covering the injector 18 and a release latch 14 for releasing the injector from an opening 16 within the case. A mobile device 20 is shown in the case 10.

Figure 6:
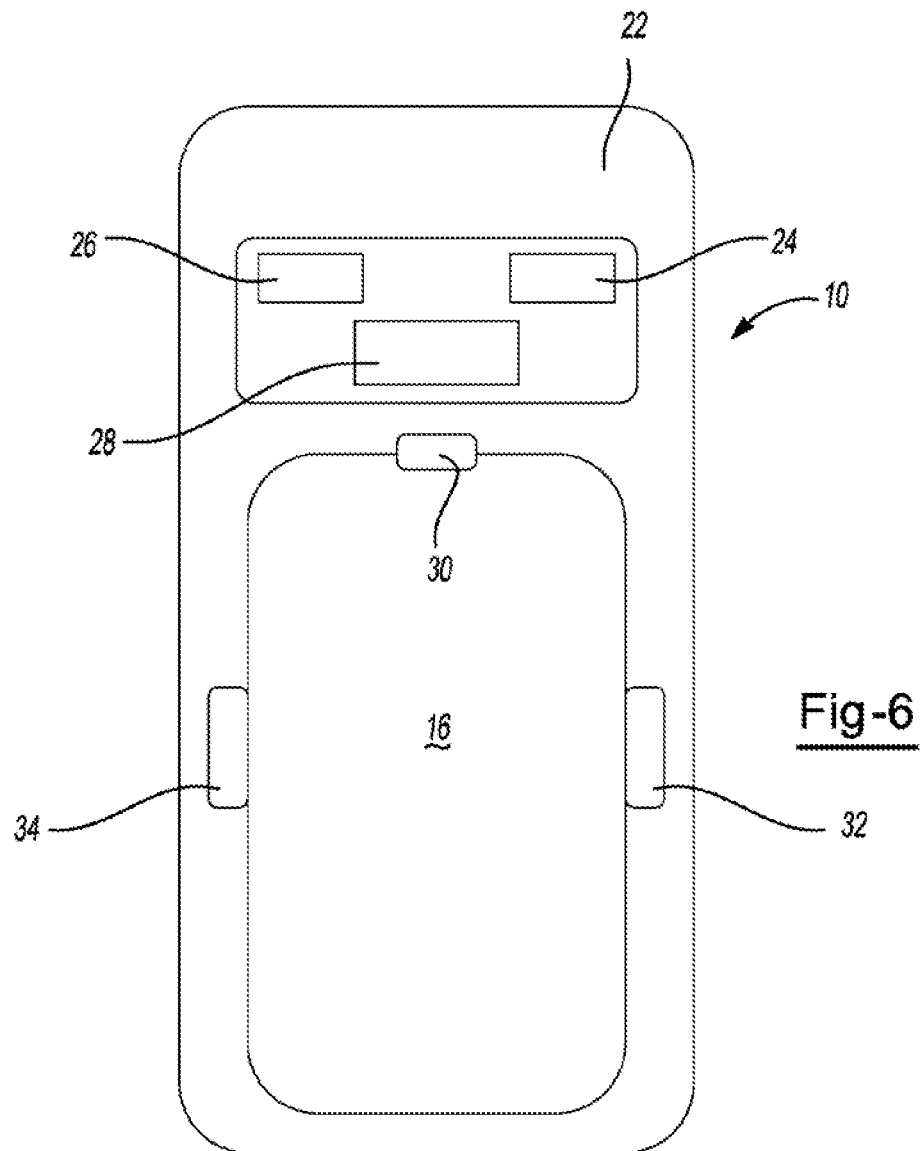
FIG. 6 shows a top down view of an exemplary phone case in accordance with the present teachings.
Figure 7:
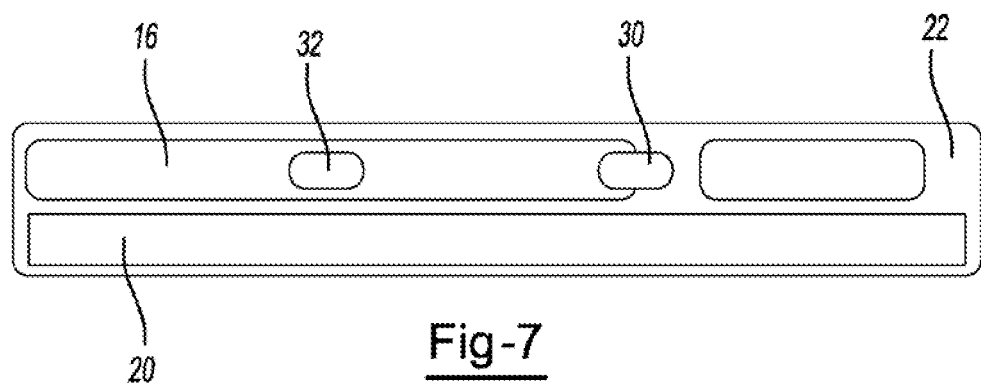
FIG. 7 shows a side profile view of phone case of FIG. 6.

FIGS. 6 and 7 depict additional components that may be included in the phone case 10. The opening 16 for receiving the injector is shown including a temperature sensor 32, a thermal fuse 34, and a cartridge sensor 30. Located remote from the injector but on the back section 22 of the case is a Bluetooth communication device 24, a microcontroller 26 and a battery 28 for the case itself. The mobile device 20 is shown at FIG. 7.

Figure 8:
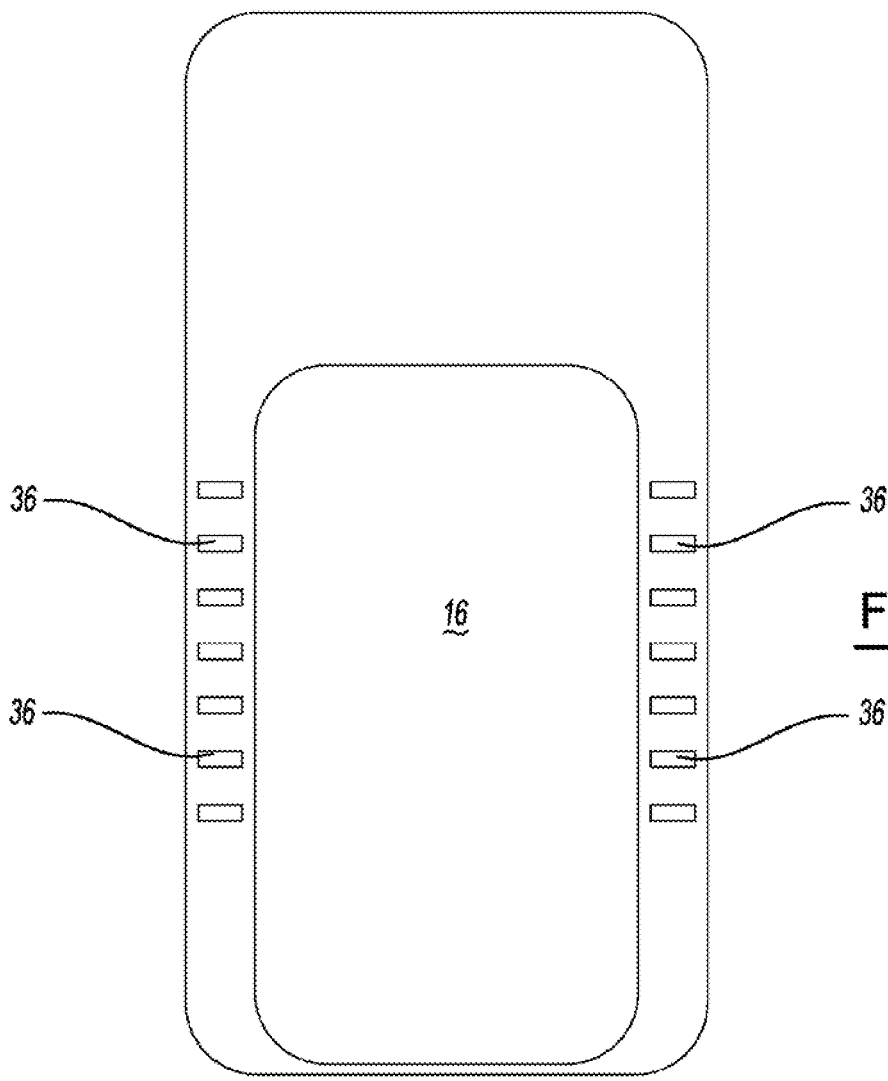
FIG. 8 shows a top down view of an exemplary phone case in accordance with the present teachings.
Figure 9:
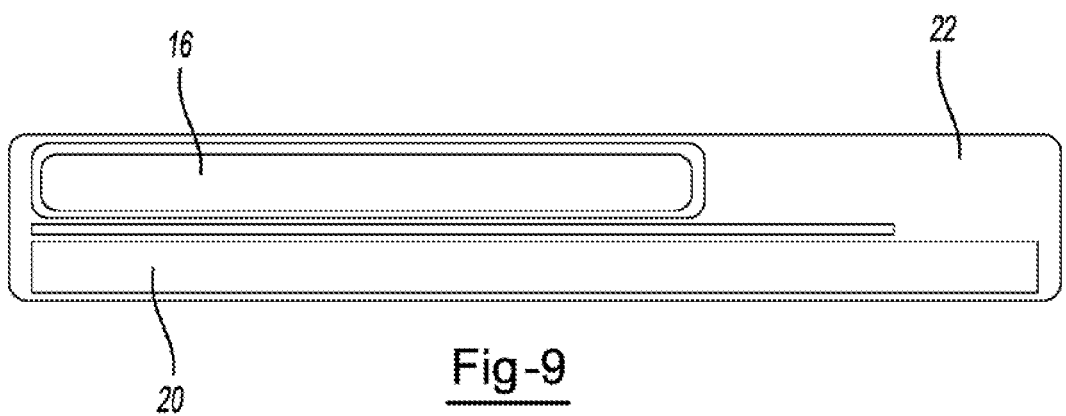
FIG. 9 shows a side profile view of the phone case of FIG. 8.
Figure 10:
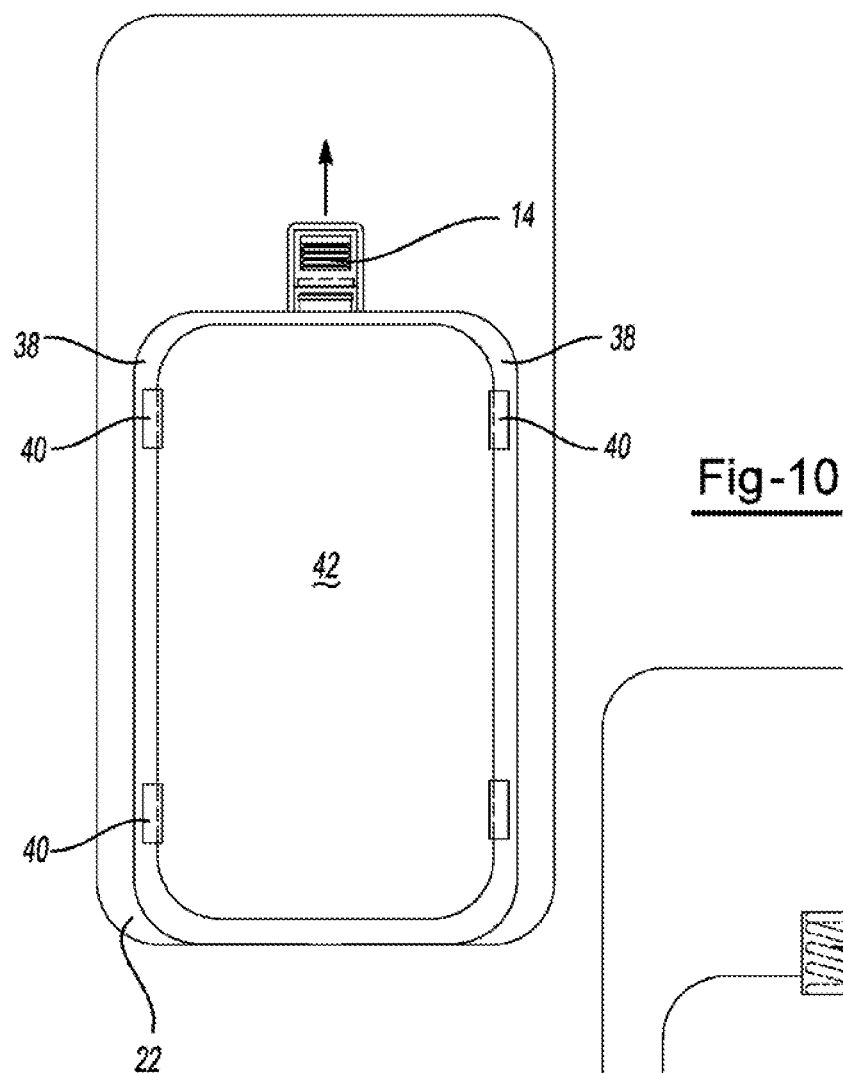
FIG. 10 shows a top down view of an exemplary phone case in accordance with the present teachings.
Figure 11:
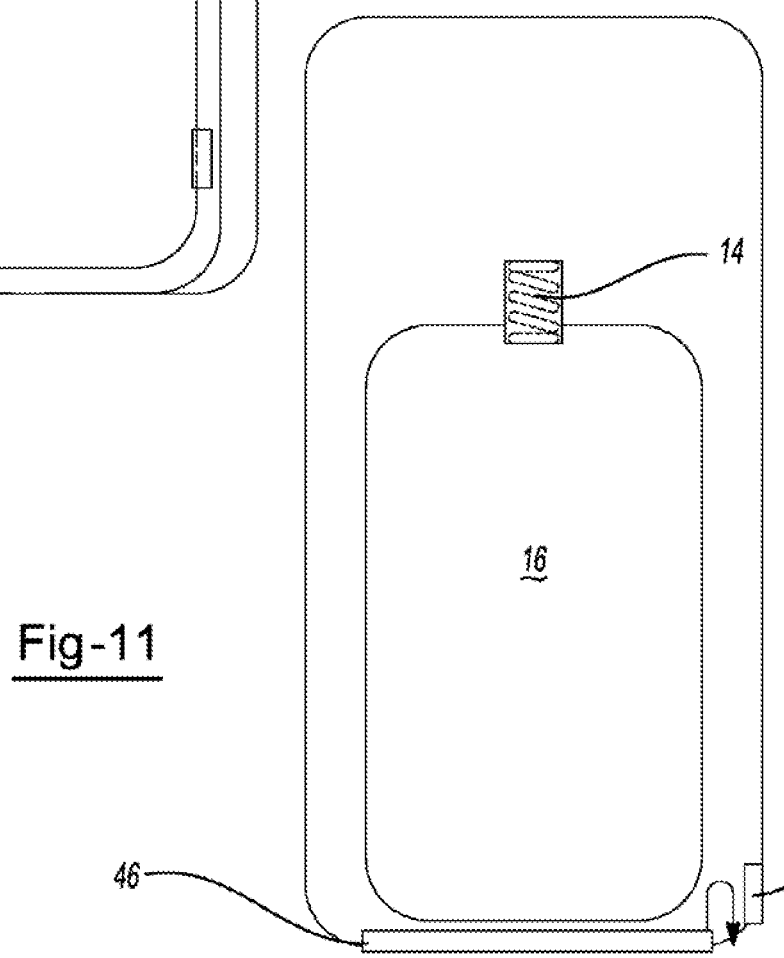
FIG. 11 is a top down view of the phone case of FIG. 10 with a portion removed.
Figure 12A:
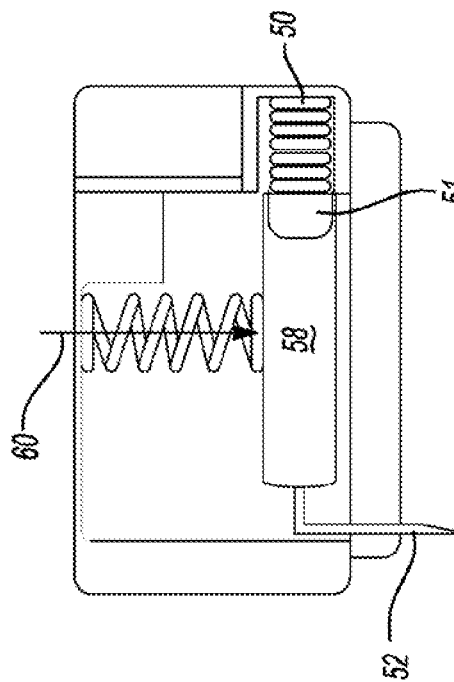
FIG. 12A is a cross section view of an exemplary injector in accordance with the present teachings.
Figure 12B:
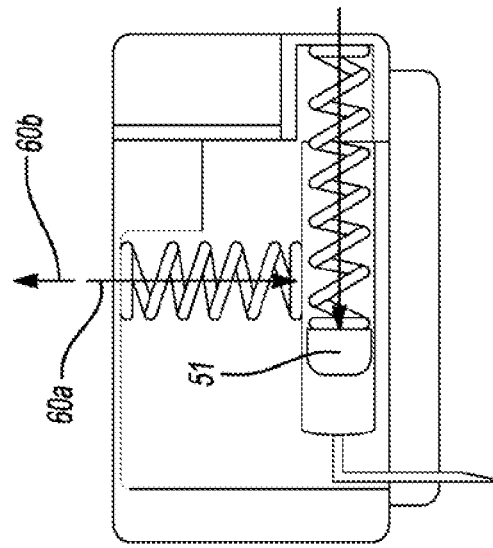
FIG. 12B is a cross section view of the injector of FIG. 12A.
Figure 12C:
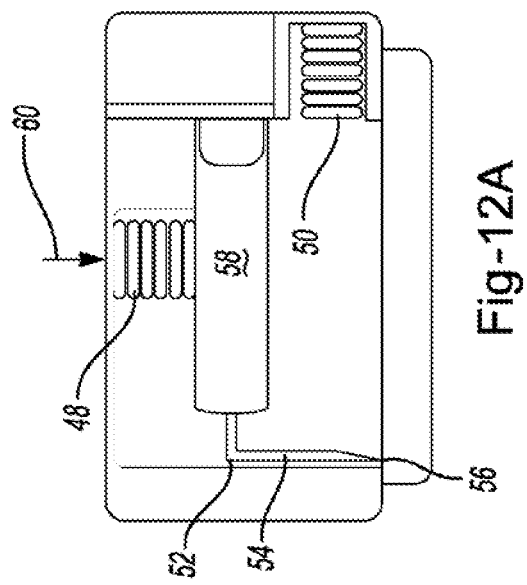
FIG. 12C is a cross section view of the injector of FIG. 12A.
Figure 12D:
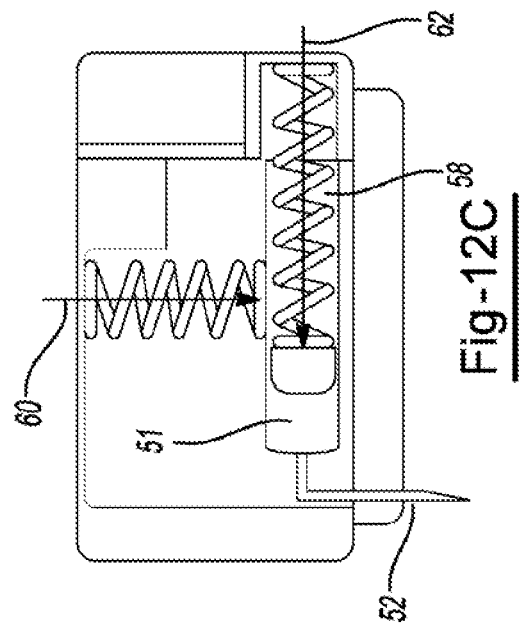
FIG. 12D is a cross section view of the injector of FIG. 12A.

FIGS. 8 and 9 depict a case including a plurality of vents 36 adjacent the opening 16 for receiving the injector. FIGS. 10 and 11 show an additional embodiment of the case including a plurality of tabs 40 and a seal 38 about the injector. A back panel 42 is shown for carrying the tabs 40 and seal 38. The back panel is shown arranged over the opening 16 for receiving the injector. A lock 44 is shown for maintaining the injector within the case. A door 46 is shown for accessing the injector.

It is possible that the injector may be designed specifically for the phone case, as shown in FIGS. 12A-12D and 13A-13C. More specifically, as shown in FIGS. 12A-12D, the injector includes springs 48, 50. The springs 48 react to a force 60 (60a) exerted on the springs causing a cartridge 58 containing medication 51 to move toward springs 50 for causing the medication to be moved via the spring force 62 and to be expelled through the needle 52 (shown including a shaft 54 and bevel 56). As the cartridge 58 moves, the needle 52 also moves forward out if the injector. Once the medication is injected, a counter force 60b causes the needle 52 to retreat back into the injector.

Figure 13A:
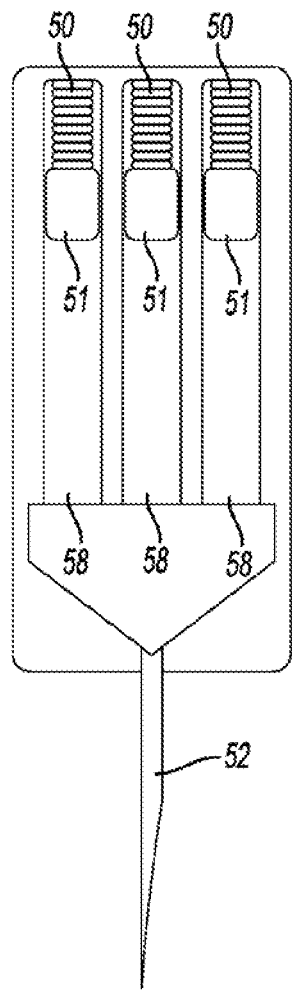
FIG. 13A is a cross section view of an exemplary injector in accordance with the present teachings.
Figure 13B:
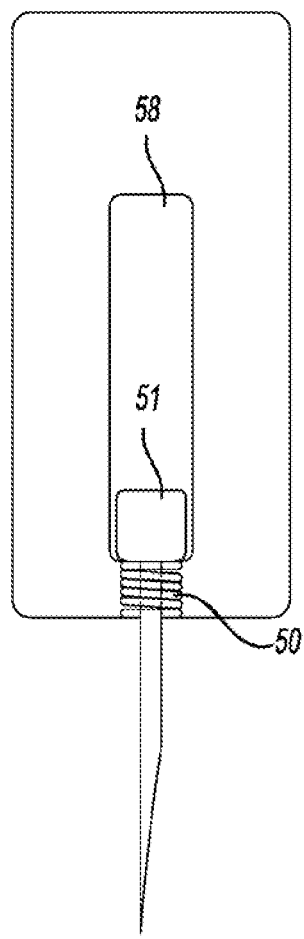
FIG. 13B is a cross section view of an exemplary injector in accordance with the present teachings.
Figure 13C:
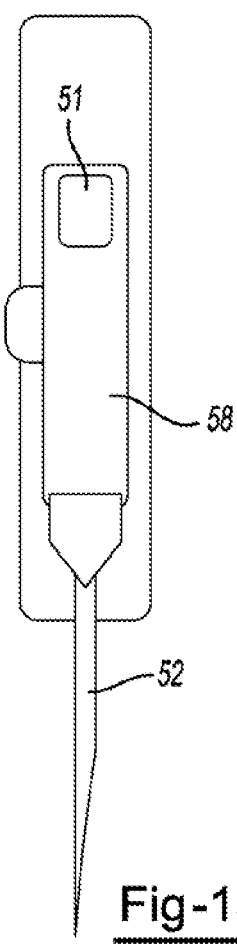
FIG. 13C is a cross section view of an exemplary injector in accordance with the present teachings.

FIGS. 13A-13C depict a variety of cartridge 58 and spring 50 arrangements including medication 51 and needles 52 associated with the injectors.

Figure 14:
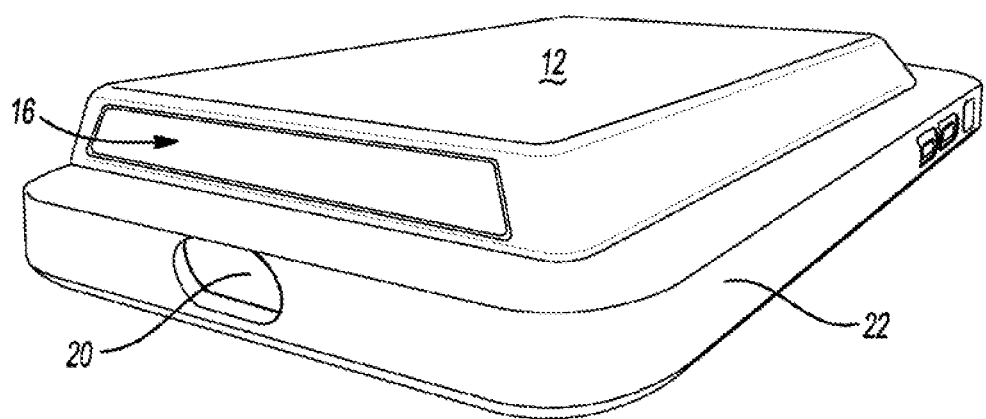
FIG. 14 is rear elevational view an of an exemplary phone case in accordance with the present teachings.
Figure 15:
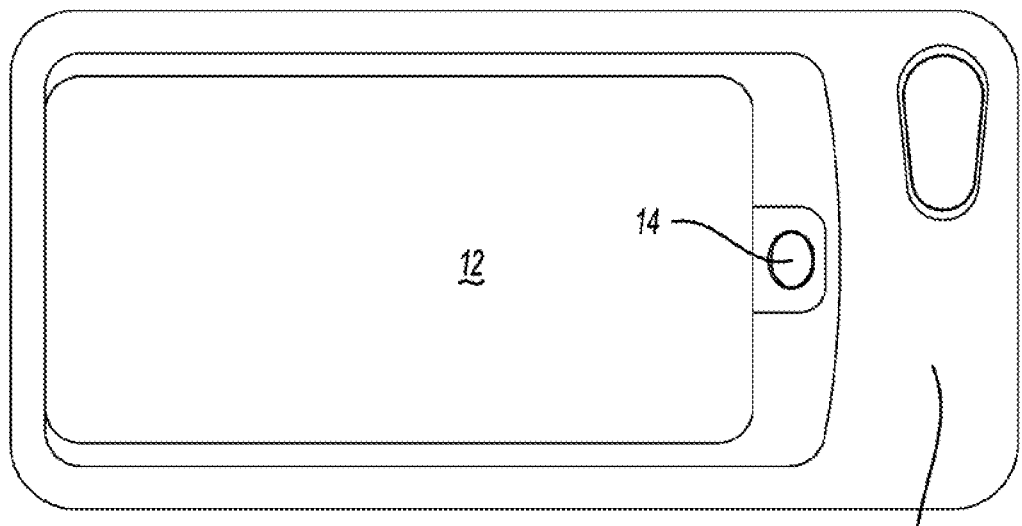
FIG. 15 is a top down view of the phone case of FIG. 14.

FIGS. 14 and 15 show an alternative embodiment of the present teachings, including a mobile device 20 shown within a case having an opening 16 for receiving an injector, a cover 12 for the injector and a back section 22 for connecting to the cover and for receiving the mobile device 20. A release latch 14 is also shown.

Figure 17A:
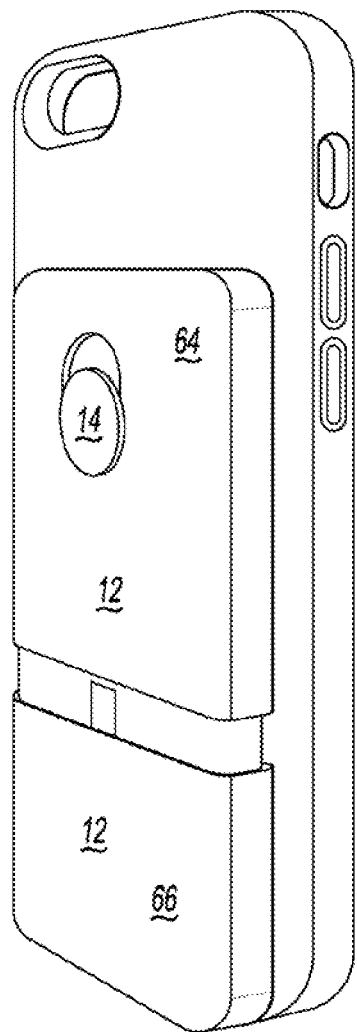
FIG. 17A is a perspective view of the phone case of FIG. 16A.
Figure 17B:
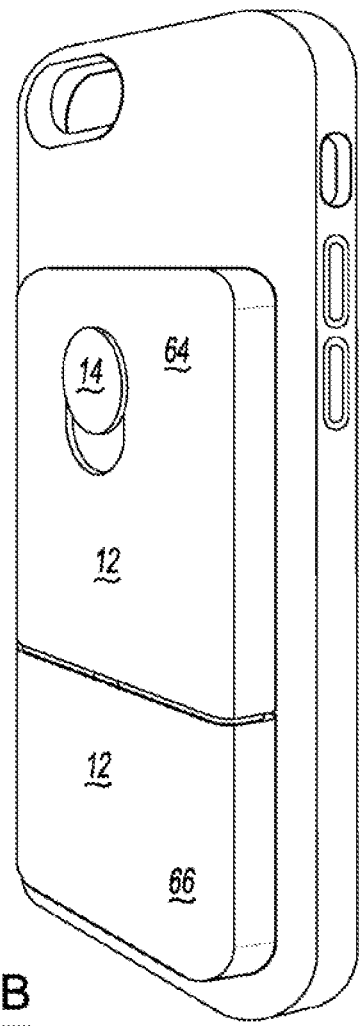
FIG. 17B is a perspective view of the phone case of FIG. 16A.
Figure 18:
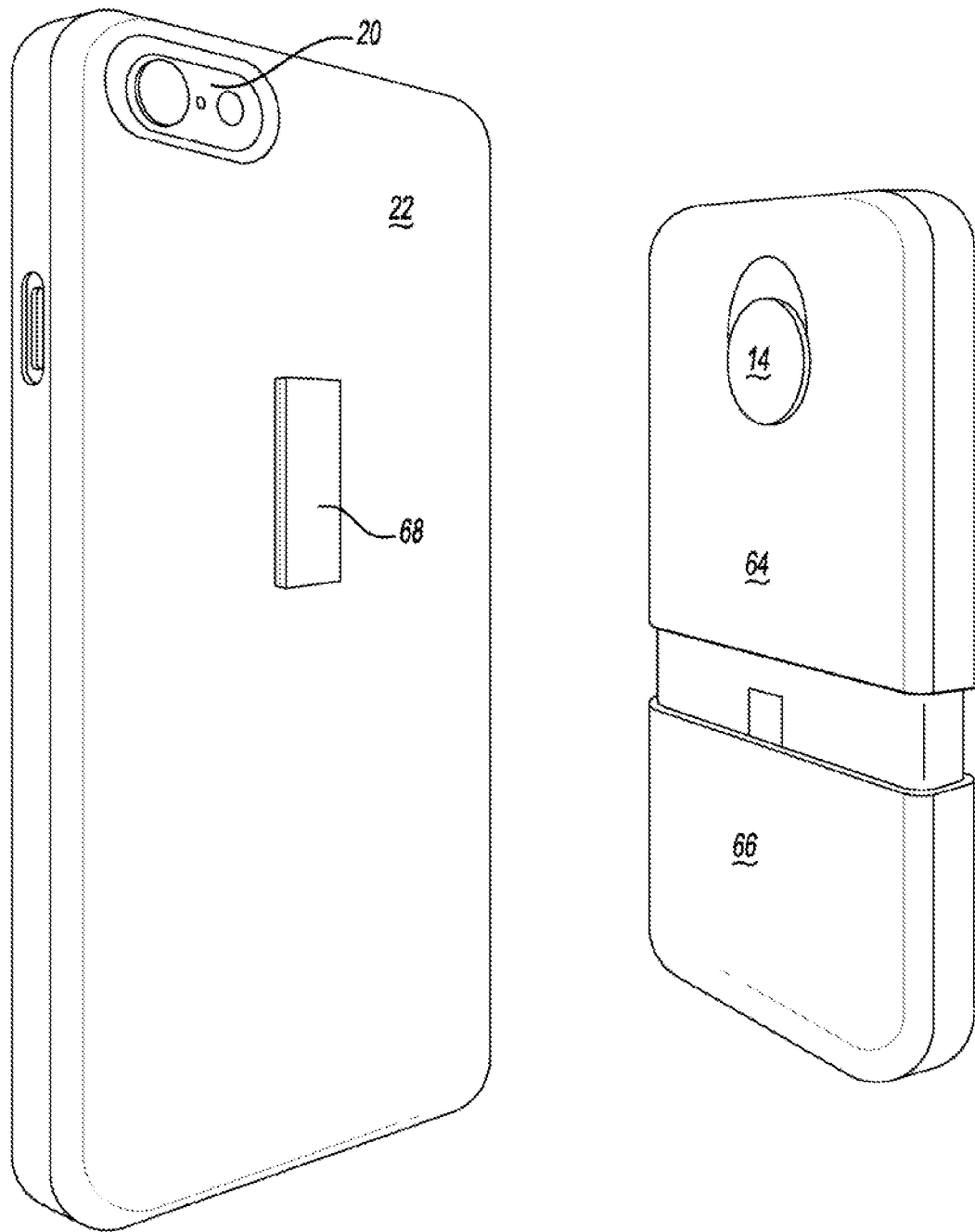
FIG. 18 is a perspective view of the phone case of FIG. 16A shown in a separated arrangement.
Figure 19:
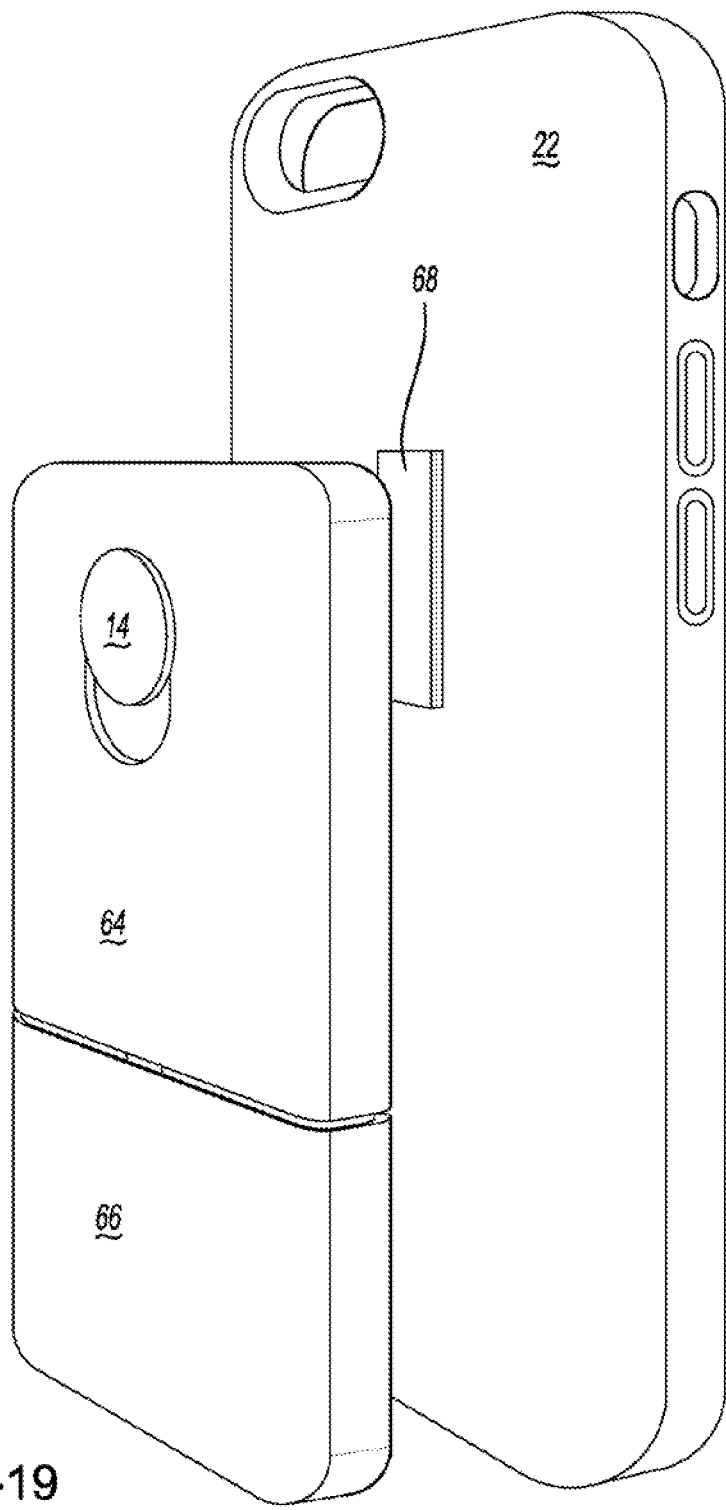
FIG. 19 is a perspective view of the phone case of FIG. 16A shown in a separated arrangement.

FIGS. 16A, 16B, 17A, 17B, 18 and 19 show an additional embodiment of the present teachings. The phone case is shown including a back section 22 for receiving a mobile device 20. The back section 22 is removably connected to a front section (e.g., cover) 12 including a first front section 64 and a second front section 66. A release latch 14 is located onto the first front section 64. The first front section 64 and second front section 66 can be separated from one another as shown in FIG. 17A, revealing an injector located therein. Movement of the release latch 14 (see FIGS. 17A and 17B) determines whether the first and second front portions are in a disconnected position (17A) or a connected position (17B). A connector portion 68 connects the front section 12 to the back section 22.

As used herein, unless otherwise stated, the teachings envision that any member of a genus (list) may be excluded from the genus; and/or any member of a Markush grouping may be excluded from the grouping.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist of, or consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. A mobile device accessory system comprising:
 a case portion including a space for receiving a mobile device and a plurality of venting ports;
 one or more sections for receiving a medication-containing device, the one or more sections separately formed from the case portion;
 a connector portion for connecting the one or more sections for receiving a medication-containing device to the case portion, the connector portion adapted for mechanical connection, magnetic attachment, adhesive attachment, or some combination thereof so that the entirety of the one or more sections for receiving a medication-containing device are separable from the case portion;
 a mobile application adapted for communication with the case portion via radio frequency;
 a temperature sensing device located within the case portion;
 wherein at least a portion of the case portion comprises a polyethylene terephthalate, a polypropylene, polyamide, polyethylene, an aerogel, a silicone, a metallized polyethylene terephthalate, a metallized polypropylene, a metallized polyamide, a metallized polyethylene or some combination thereof;
 wherein the mobile application sends alert messages to emergency services and/or one or more of a user's family, friends, caregivers, medical professional that will include their current location and wherein the mobile application transmits a portion of information via a HIPAA compliant platform; and
 wherein the mobile application sends push notifications to the user regarding one or more of medication expiration or training videos for use of the medication and/or mobile application.

2. The mobile device accessory system of claim 1, including a release latch for accessing the medication.

3. The mobile device accessory system of claim 1, wherein the connector portion utilizes a friction fit for connecting the one or more sections for receiving a medication-containing device to the space for receiving a mobile device.

4. The mobile device accessory system of claim 1, wherein the mobile application is adapted for one or more of:
 (i) permitting access to the injector;
 (ii) notifying a user's care circle if the injector has been accessed;
 (iii) notifying a user if the medication within the injector is expired;
 (iv) notifying a user if the injector has malfunctioned; or
 (v) notifying a user if the temperature within the case portion exceeds a predetermined temperature limit.

5. The mobile device accessory system of claim 1, wherein the system includes more than one dose of medication.

6. The mobile device accessory system of claim 1, wherein the mobile application transmits a portion of information via a HIPAA compliant platform.

7. The mobile device accessory system of claim 1, wherein the mobile application is adapted to scan food product barcodes to access ingredient information.

8. The mobile device accessory system of claim 1, wherein the mobile application is adapted to identify ingredients in food products to which the user is allergic.

9. The mobile device accessory system of claim 1, wherein the medication is selected from insulin, epinephrine, or a medication for treating breathing issues.

10. The mobile device accessory system of claim 1, wherein the mobile application is adapted to monitor the number of remaining doses of the medication.

11. The mobile device accessory system of claim 1, including one or more subsystems selected from an electronics system, a communication system, a thermal maintenance system, a security system, or any combination thereof.

12. The mobile device accessory system of claim 1, including an electronics sub-system including one or more of microcontrollers, power sources, circuit boards, fuses, switches, sensing devices, or any combination thereof.

13. The mobile device accessory system of claim 1, including one or more microcontrollers comprising one or more peripherals selected from a Universal Asynchronous Receiver Transmitter (UART), Universal Synchronous/Asynchronous Receiver Transmitter (USART), Inter-Integrated circuit (I2C), Analog to Digital Converter (ADC), or any combination thereof.

14. The mobile device accessory system of claim 1, wherein the temperature sensing device is selected from an analog sensor, digital sensor, diode sensor, thermistor sensor, resistive temperature detector, or any combination thereof.

15. The mobile device accessory system of claim 14, including a medical device sensor capable of sensing introduction, presence, and/or removal of a medical device.

16. The mobile device accessory system of claim 15, wherein the medical device sensor includes a switch contact, optical beam break, capacitive sensor, inductive sensor, or any combination thereof.

17. The mobile device accessory system of claim 1, including a thermal maintenance system that reflects and dissipates heat and radiation from the device accessory system.

18. The mobile device accessory system of claim 17, wherein the thermal maintenance system includes one or more of a heat exchanger, Peltier device, fan, or any combination thereof.

19. The mobile device accessory system of claim 1, including a cartridge sensor that senses the presence and/or absence of medication.

20. The mobile device accessory system of claim 1, wherein the one or more sections for receiving a medication-containing device include a first front section and a back front section and the medication can be accessed by at least partially separating the first and second front sections from one another.

* * * * *